(12) United States Patent
Hansson

(10) Patent No.: US 6,520,945 B1
(45) Date of Patent: Feb. 18, 2003

(54) SHAPE-STABLE ABSORBENT ARTICLE

(75) Inventor: Roy Hansson, Mölndal (SE)

(73) Assignee: SCA Hygiene Products AB, Göteborg (SE)

(*) Notice: Subject to any disclaimer, the term of this patent is extended or adjusted under 35 U.S.C. 154(b) by 0 days.

(21) Appl. No.: 09/446,398

(22) PCT Filed: Aug. 4, 1998

(86) PCT No.: PCT/SE98/01434

§ 371 (c)(1),
(2), (4) Date: Dec. 22, 1999

(87) PCT Pub. No.: WO99/08639

PCT Pub. Date: Feb. 25, 1999

(30) Foreign Application Priority Data

Aug. 20, 1997 (SE) ............................................. 9702999

(51) Int. Cl.⁷ ................................................. A61F 13/15
(52) U.S. Cl. .............................. 604/385.24; 604/385.31
(58) Field of Search ................. 604/369, 378, 604/379, 380, 385.01, 385.101, 385.24, 385.31

(56) References Cited

U.S. PATENT DOCUMENTS

| 4,323,070 A | * | 4/1982 | Ternstrom et al. ........ 128/287 |
|---|---|---|---|
| 4,895,568 A | | 1/1990 | Enloe .................... 604/385.2 |
| 4,897,084 A | | 1/1990 | Ternström et al. ....... 604/385.2 |
| 5,300,055 A | | 4/1994 | Buell .................... 604/385.1 |
| 5,591,150 A | * | 1/1997 | Olsen et al. ............ 604/385.1 |
| 5,795,345 A | * | 8/1998 | Mizutani et al. ............ 604/380 |

FOREIGN PATENT DOCUMENTS

| EP | 0 091 412 | 5/1987 |
|---|---|---|
| GB | 2 284 537 | 6/1995 |
| WO | 04/10956 | 5/1994 |
| WO | 94/10953 | 5/1994 |
| WO | 95/31162 | 11/1995 |

* cited by examiner

*Primary Examiner*—Dennis Ruhl
*Assistant Examiner*—Jamisue A. Webb
(74) *Attorney, Agent, or Firm*—Burns, Doane, Swecker & Mathis, LLP

(57) ABSTRACT

An absorbent article with a longitudinal direction and a transverse direction, at least one elastic member (14) being arranged with prestressing in the crotch area (8) of the article, extending essentially in the transverse direction of the article. The elastic member (14) is arranged between the liquid-permeable surface layer (2) of the article and its absorption body (4) on a first surface of the absorption body (4). A shaping element (16) which is rigid to bending in the transverse sense of the article is arranged on a second surface of the absorption body (4), the shaping element (16) counteracting contraction of the elastic member (14).

14 Claims, 3 Drawing Sheets

SHAPE-STABLE ABSORBENT ARTICLE

TECHNICAL FIELD

The present invention relates to an absorbent article such as an incontinence protector, a sanitary towel or a diaper. The article comprises a liquid-permeable cover layer, a liquid-impermeable cover layer, and an absorption body enclosed between the two cover layers, and at least one elastic member which is arranged with prestressing in the crotch area of the article, extending essentially in the transverse direction of the article, between the side edges of the article.

BACKGROUND

On use of absorbent articles which are intended to be used for absorption of bodily excretions such as urine and menstruation blood, it has been found that leakage sometimes occurs on account of liquid flowing across the surface of the article and running out past its edges instead of being absorbed into the article. This problem is especially evident in connection with incontinence protectors for adults suffering from urinary incontinence. On urinating, the incontinent subject excretes a relatively large amount of urine within a short period of time. It can therefore happen that not all the liquid has time to penetrate into the incontinence protector. The excess liquid will thus flow across the surface of the article and run out onto the user's clothes. Since the urine impacts the surface of the incontinence protector at relatively high pressure, this also means that there is a risk of the urine simply rebounding off the surface of the incontinence protector and then running out from the incontinence protector.

In order to avoid leakage of liquid caused by the liquid running across the surface of an absorbent article instead of penetrating into the article, it has been proposed that the surface of the article be pleated. By doing so, on the one hand, an increased liquid-receiving capacity of the article is achieved, and, on the other hand, the folds in the surface of the article make it difficult for the liquid to flow freely across the surface. One method of producing pleats in the surface of an absorbent article is to provide the article with transverse elastic members which are secured to the article in a prestressed state. Such transverse elastic means are described in U.S. Pat. No. 4,323,070. By arranging transverse elastic means in an absorbent article, the article is also curved into a liquid-receiving cup shape.

Other methods for creating liquid-receiving cup-shaped spaces are described, for example, in documents EP 0,091,412, U.S. Pat. No. 4,897,084 and WO 95/31162. Although these previously known articles do afford increased safety against leakage, there is nevertheless still a need for further improvements.

A disadvantage of the previously known cup-shaped absorbent articles is in fact that while they are being used, they may deform to such an extent that the cup shape is lost. Such deformation is particularly noticeable and troublesome in connection with so-called light incontinence protectors. Light incontinence protectors are relatively small absorbent articles which are worn inside a pair of ordinary underpants. Light incontinence protectors are often used by healthy individuals who are professionally and socially active. It is therefore extremely important that the articles should be small and discreet so that they can be concealed under normal clothes. At the same time, of course, it is essential that the articles have a high absorption capacity and do not leak.

Light incontinence protectors and sanitary towels are generally secured in the crotch area on the user's underwear by means of special self-adhesive surfaces which are arranged on that side of the protector or sanitary towel which is facing the underwear during use. Upon use, the absorbent article will be pressed together in order to fit in the confined space between the user's legs. In doing so, the article is deformed and pleated in an uncontrolled manner, which often adversely affects both the absorption capacity and the ability to quickly admit the excreted body fluid. For example, it is not unusual for the edge portions to be folded in across the liquid-permeable surface layer, so that the surface which in practice is available to receive liquid is greatly reduced. When the user is moving, for example walking or running, mechanical shaping of the article takes place, which not infrequently results in the absorption body of the article bunching together and forming cracks. Of course, such deformation also has an adverse effect on the function of the article.

BRIEF DESCRIPTION OF THE INVENTION

With the present invention, however, it has been possible to obtain an absorbent article which is of the type mentioned in the introduction, and in which article the disadvantages associated with the previously known articles of this kind have been largely eliminated. An article according to the invention is distinguished primarily by the fact that at least one elastic member is arranged between the liquid-permeable surface layer and the absorption body on a first surface of the absorption body, and also by the fact that a shaping element which is rigid to bending in the transverse sense of the article is arranged between the side edges of the article on a second surface of the absorption body, the shaping element counteracting contraction of the elastic member.

By arranging a component which is rigid to bending, and which to a certain extent counters the contracting force in the elastic member, the article is prevented from crumpling together in an uncontrolled manner during use. Instead, a well-defined bending and cup shape are obtained, in which cup the excreted body fluid can be caught and can then be absorbed into the article. The shaping element also contributes to increasing the stability of the absorption body of the absorbent article and thus prevents the absorption material from bunching together or cracking.

The shaping element is advantageously elastic to bending so that its shape can be continuously adapted to changes in the forces occurring during use of the article. By using a shaping element which is elastic to bending, the article, after compression in the transverse sense, can at least substantially resume its original shape.

A material which in this connection has been found to function particularly well when used in the shaping element is a layer of foam material. Such a foam material can also be used as the liquid-impermeable cover layer of the article and thus serves at the same time as the shaping element.

Another type of material which can be used as the shaping element is strongly compressed fibre layers, for example of the type described in documents WO 94/10953 and WO 94/10956. Such fibre materials have a density of up to at least 0.1 g/cm$^3$.

To make it easier for the article to be bent into a cup shape through the cooperation between the elastic member and the shaping element, it can be an advantage if the absorption body has bend notches. Such bend notches can consist, for example, of recesses in the absorption body, as a result of which the absorption body can be curved without folds or cracks forming in an uncontrolled way in the absorption material. Alternatively, the bend notches can consist of slits or compressions in the absorption body. It is also possible to provide the liquid-permeable cover layer with corresponding bend notches.

Similarly, the shaping element can of course also have bend notches.

To obtain a larger cup shape, or to form a cup with different depths in different parts of the absorbent article, a plurality of elastic members in the form of strings, bands or the like can be arranged between the side edges of the article. The elastic members can in this case be arranged with the same prestressing or with different prestressing from each other.

The elastic element or elements do not have to be arranged entirely in the transverse direction of the article. However, it is necessary for a contracting force to be generated in the transverse direction of the article.

Moreover, the shaping element can consist of two or more parts or "ribs" which are separated in the longitudinal direction of the article. Each part of the shaping element extends between the side edges of the article. An advantage of such an arrangement is that the article acquires greater flexibility in the longitudinal sense and thus shapes more easily to the contour of the user's body. In addition, the article can more easily be folded when packing an unused article, and also after use, when the article is to be discarded.

BRIEF DESCRIPTION OF THE FIGURES

The invention will be described in greater detail below, with reference to the figures shown on the attached drawings, where.

DESCRIPTION OF ILLUSTRATIVE EMBODIMENTS

Figure 1:
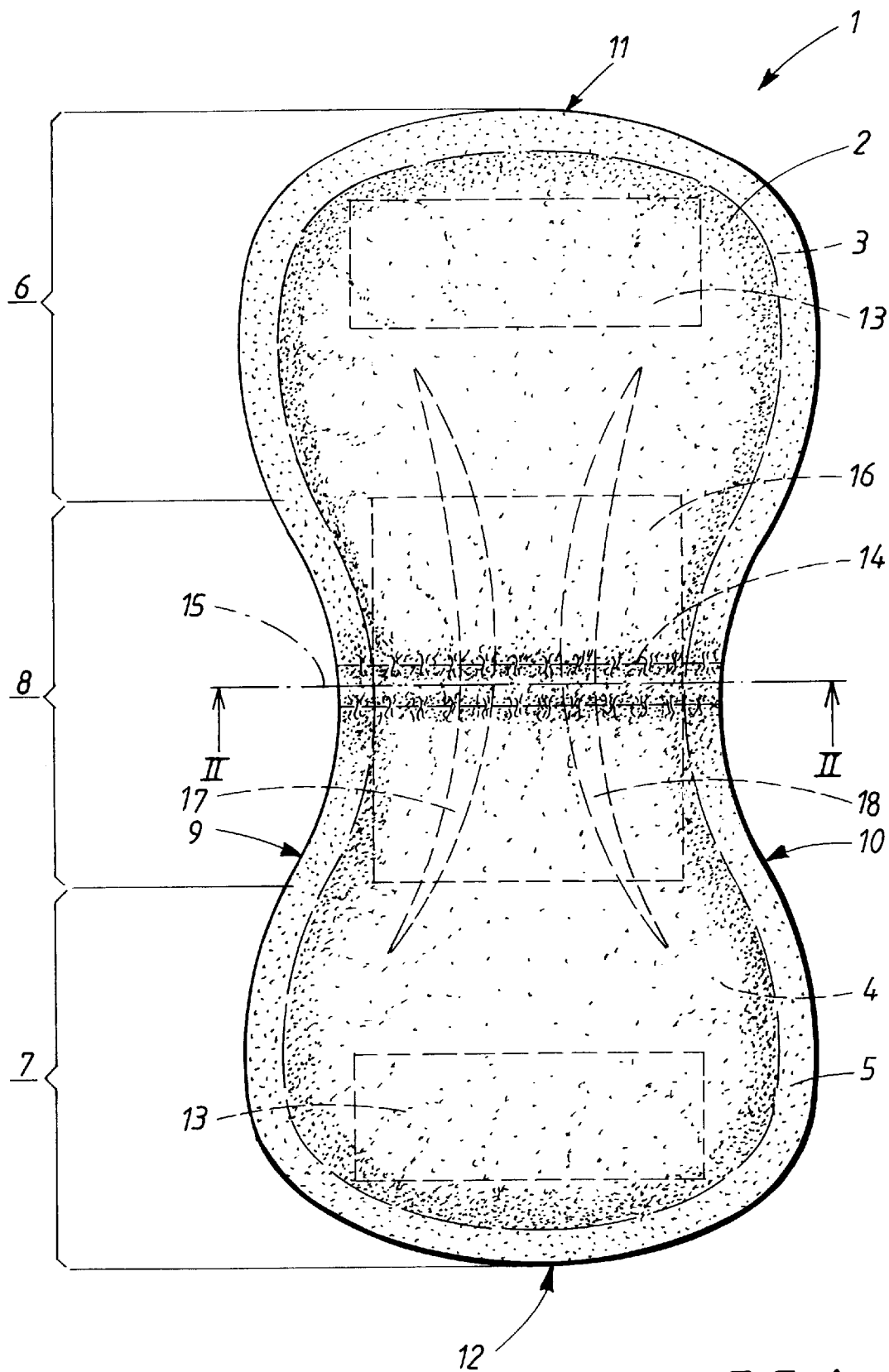
FIG. 1 is a plan view of an incontinence protector according to a first embodiment of the invention, seen from that side which is intended to be directed towards the user during use.

The incontinence protector 1 shown in FIG. 1 comprises a liquid-permeable cover layer 2, arranged on that side of the incontinence protector 1 intended to be directed towards the user during use, a liquid-impermeable layer 3, arranged on that side of the incontinence protector 1 intended to be directed away from the user during use, and an absorption body 4 enclosed between the two cover layers 2, 3.

The material of the liquid-permeable cover layer 2 can, for example, be a perforated plastic film, a net of plastic or textile material, a nonwoven material, or a laminate of two or more such layers of material. The plastic materials used in the liquid-permeable surface material are generally thermoplastics, such as polyethylene, or polypropylene. The expression nonwoven material is intended to mean nonwoven fibre fabrics. Suitable nonwoven materials can consist of natural fibres, such as cellulose or cotton, or of synthetic fibres, such as polyethylene, polypropylene, polyester, polyurethane, nylon, or regenerated cellulose. It is also possible, of course, to use nonwoven materials produced from fibres with two or more components included, and mixtures of different fibre types.

The liquid-permeable cover layer 2 is intended to admit liquid and convey it into the absorption body 4. Moreover, the cover layer 2 should be soft and comfortable against the user's body, and should be able to prevent so-called rewetting, i.e. absorbed body fluid forcing its way back towards the user's skin. For reasons of comfort, and in order to prevent skin irritation, it is important that the surface on the part of the incontinence protector 1 lying against the user's skin should be kept as dry as possible during use. A dry surface of the incontinence protector is also fresher and more comfortable for the user during use and is, both purely visually and when handling the incontinence protector when it is to be changed, more acceptable than a wet surface.

The liquid-impermeable cover layer 3 consists of a liquid-impermeable material. Thin, liquid-impermeable plastic films are suitable for this purpose. However, it is also possible to use material which at the outset is liquid-permeable, but which has been provided with a coating of plastic, resin or other liquid-impermeable material. In this way, leakage of liquid from the underside of the absorbent article is prevented. The liquid-impermeable cover layer 3 can thus consist of any material which is compatible with the skin and which satisfies the criterion of liquid-impermeability. Examples of materials which are suitable as barrier layers are plastic films, nonwoven materials and various types of laminates. Examples of plastic films that can be used are those consisting of polyethylene, polypropylene or polyester. Alternatively, the liquid-impermeable cover layer 3 can consist of a laminate of a liquid-impermeable plastic layer, directed towards the absorption body, and a nonwoven layer directed towards the user's underclothes. Such a structure creates a leak-tight barrier layer with a textile feel.

The absorption body 4 can advantageously be made up essentially of cellulose fluff pulp. This can be in the form of rolls, bales or sheets which are defibred in the dry and converted in the fluffed form to a pulp sheet, with or without admixture of so-called superabsorbents, which are polymers with the ability to absorb several times their own weight of water or body fluid. Examples of other materials that can be used are various types of natural fibres, such as cotton fibres, peat moss or the like. It is of course also possible to use absorbent synthetic fibres, or mixtures of natural fibres and synthetic fibres. The absorption material also contains further components, such as members for diffusing the liquid, or binders such as, for example, thermoplastic fibres which have been heat-treated to hold short fibres and particles together in one continuous unit. It is also possible to use different types of absorbent foam material in the absorption body 4. The absorption body 4 can consist of one continuous layer or can be made up of a plurality of different layers or parts.

The two cover layers 2, 3 are connected to each other outside the absorption body 4 and form a projecting margin 5 around the entire periphery of the incontinence protector 1. The cover layers 2, 3 are joined in any appropriate manner, such as by adhesive bonding, stitching, or welding with heat or ultrasound.

The incontinence protector 1 is essentially hourglass-shaped and has two end portions 6, 7 which, during use, are intended to be directed forwards and rearwards on the user, and also an intermediate narrower crotch portion 8 which is intended to be arranged at the user's crotch. The incontinence protector 1 also has two inwardly curved side edges 9, 10 and two outwardly curved end edges 11, 12.

The division of the incontinence protector 1 into two end portions 6, 7 and a crotch portion 8 must not be regarded as meaning that there are sharp boundaries between the different portions 6–8, but is intended principally to facilitate the description of the incontinence protector 1 on the basis of the differences which exist between the different portions 6–8 as to how they are intended to be placed in relation to a user's body. Thus, the transition between the different portions 6–8 does not occur at defined transverse lines, but rather within transition areas situated at a distance of about a third of the length of the incontinence protector from each end edge 11, 12. The crotch portion 8 thus constitutes that part of the incontinence protector which, during use, is intended to receive and absorb most of the excreted body fluid.

So that it can be secured inside a pair of underpants, the incontinence protector 1 is provided with securing members 13 in the form of self-adhesive surfaces arranged on the end portions 6, 7 of the incontinence protector. The invention must not of course be regarded as being limited to the use of adhesive securing members, or to the specific adhesive pattern shown in FIG. 1. Thus, securing adhesive can be arranged over the whole surface of the liquid-impermeable cover layer 3 which is intended to be directed towards the user's underpants, or can be arranged in the form of longitudinal strips, spots or other suitable patterns. The incontinence protector can be provided alternatively, or in combination with an adhesive securing means, with mechanical securing means such as snap fasteners, clips or the like. In addition, it is possible to use friction-enhancing elements such as elastic coatings, foam layers, nonwoven layers or the like.

An elastic member 14 in the form of a tape of elastic material such as rubber, elastic nonwoven, polyurethane or the like, is arranged along the transverse centre line 15 of the incontinence protector 1. The elastic member 14 extends between the side edges 9, 10 of the incontinence protector and is secured between the two cover layers 2, 3 in the projecting margin 5. The elastic member can also be secured to a component in the absorption body 4 and/or the liquid-permeable cover layer 2. Because the elastic member 14 is secured to the incontinence protector 1 in the stretched-out state, the elastic member 14 seeks to recover its unstretched state. In so doing, the crotch portion 8 of the incontinence protector is curved into a cup-like shape, as can best be seen in FIG. 2.

To obtain a controlled and well-defined shaping of the incontinence protector, and to avoid undesired deformation and crumpling of the protector, a shaping element 16 which is rigid to bending is arranged between the liquid-impermeable cover layer 3 and the absorption body 4. The shaping element advantageously comprises a rigid and elastic layer of foam material or plastic and serves to counteract the contracting force of the elastic member 14. In this way, the liquid-impermeable cover layer 3 of the article can be shaped into a smooth cup, without pleats or creases. This also prevents the side edges 9, 10 of the article from being folded in across the liquid-permeable cover layer 2, since such inward-folding is counteracted by the rigid shaping element.

Figure 3:
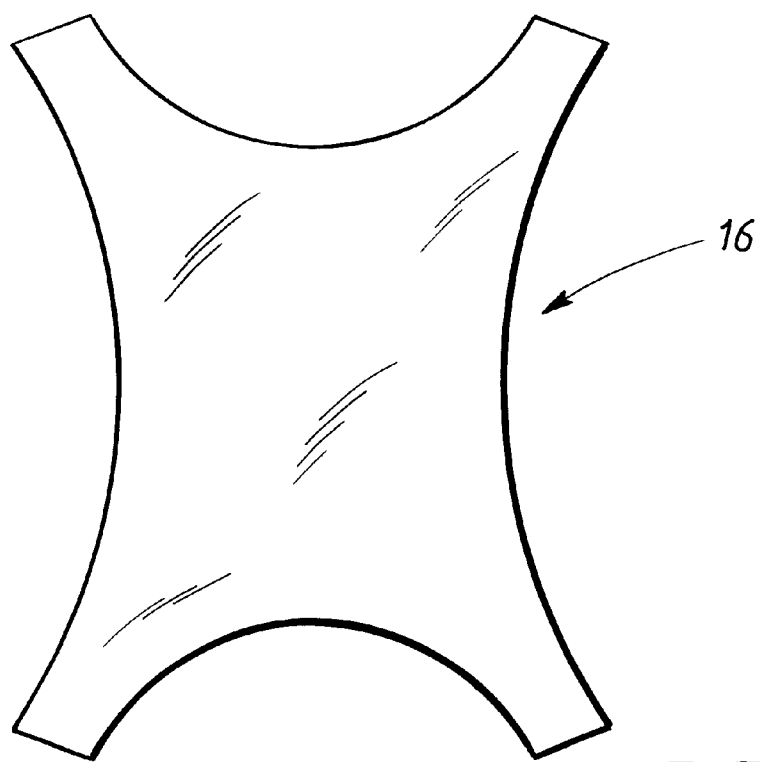
FIG. 3 is an alternative form for a shaping element according to the invention.

The shaping element 16 is shown as a rectangular sheet of material. It is of course possible for the shaping element to have another shape; for example, the shape shown in FIG. 3 can be used. Other conceivable shaping elements can comprise one or more transverse "rib-like" parts. However, the shaping element 16 must be arranged adjacent to the elastic member 14 so as to be able to cooperate with the latter.

In the example shown, the incontinence protector 1 has only one elastic member 14. It is of course possible to instead use a plurality of essentially transverse elastic members which, together with the shaping element 16, create the cup shape of the incontinence protector 1. Here, the extent of the cup formation in the crotch area 8 of the incontinence protector is controlled by the choice of number of elastic members and by the prestressing with which the elastic members have been arranged on the incontinence protector. It is possible, for example, to form a cup which is deepest at the transverse centre line 15 of the incontinence protector 1, and levels out towards the end portions 6, 7 of the incontinence protector, by using elastic members with different prestressing from each other.

Another way of controlling the bending of the incontinence protector is through the choice of material for the shaping element 16. Thus, given the same prestressing of the elastic member 14, less cup formation is obtained the stiffer the shaping element 16 is. In addition, the shaping element 16 can be provided with recesses, grooves, folds or the like, for facilitating correct bending of the incontinence protector. In this way it is also possible to use shaping elements of stiffer material than has otherwise been possible.

The shaping element 16 is advantageously made essentially of a material whose mechanical properties remain principally unaffected even after wetting. It is especially expedient for the stiffness of the material to be maintained after wetting. However, the shaping element can consist of a material which absorbs body fluid and thus gradually loses its stiffness. An example of such a material is the fibre layers which are described in WO 94/10953 and WO 94/10956. These materials are dry-formed fibre layers of high density and stiffness which are arranged in the incontinence protector without prior defibering. The described materials have sufficient stiffness to be able to cooperate with an elastic member to produce the desired cup shape. Even if a portion at the bottom of the cup loses its stiffness after a time, the stiffness in the surrounding portions of the material still remains. In most cases this is enough to ensure that the resistance to deformation of the incontinence protector will be sufficiently high during the time the incontinence protector is in use.

It is crucial to the invention that the elastic member 14 is arranged on that surface of the absorption body 4 which is intended to be directed towards the user. This means that the incontinence protector is forced to curve in such a way that a cup is formed, and not a raised mound, towards the user's body.

Figure 2:
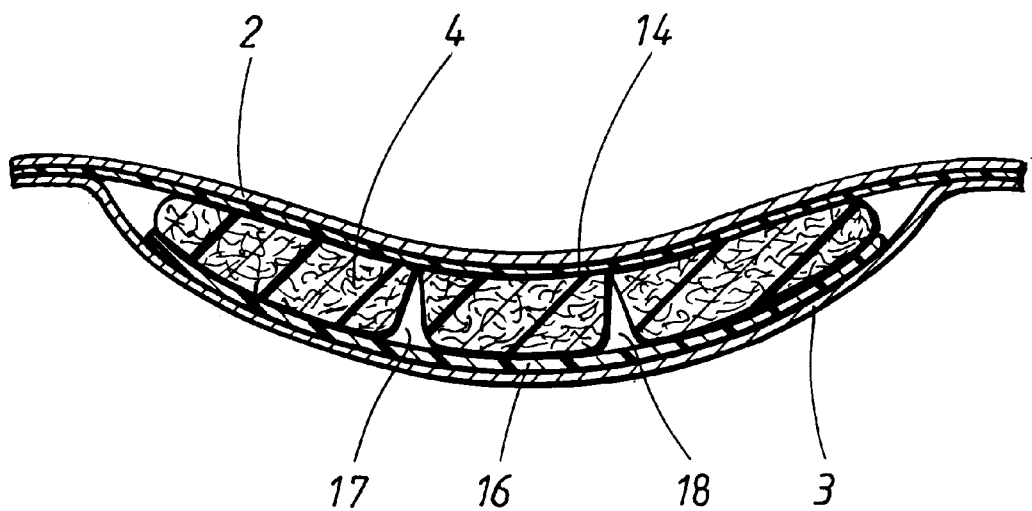
FIG. 2 is a cross-section, taken along the line II—II, through the incontinence protector in FIG. 1.

The incontinence protector 1 shown in FIGS. 1 and 2 also has crescent-shaped recesses 17, 18 which are formed in the absorption body 4. The recesses 17, 18 are intended to facilitate the transverse curvature of the absorption body 4 and to contribute to the formation of a cup-shaped space which is deepest at the crotch portion 8 of the incontinence protector 1. As the incontinence protector curves, those edges of each recess 17, 18 located at the liquid-permeable cover layer 2 are brought together, as is shown in FIG. 2. This permits a decrease in the distance between the side edges 9, 10 of the incontinence protector, without the absorption body being folded in an uncontrolled manner.

Figure 4:
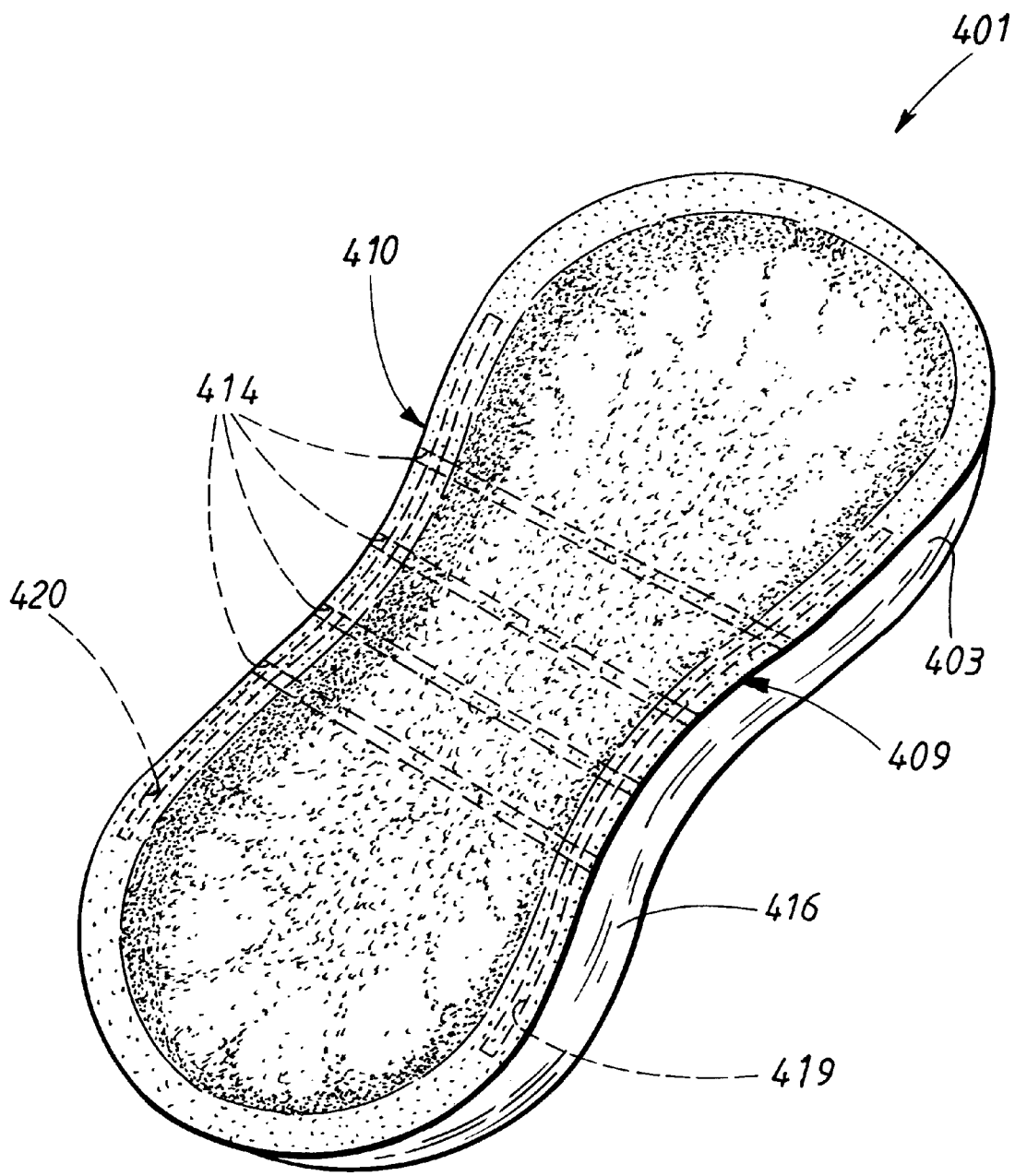
FIG. 4 is a perspective view of an incontinence protector according to a second embodiment of the invention.

In the case of the incontinence protector 401 shown in FIG. 4, the liquid-impermeable cover layer 403 consists of a material which at the same time serves as a shaping element 416. The incontinence protector 401 is provided with a number of transverse elastic members 414 in the form of strings, tapes or the like, which cooperate with the shaping element 416 in order to give the incontinence protector a cup shape. The incontinence protector also has longitudinal elastic members 419, 420 arranged along the side edges 409, 410 of the protector 401 in order to curve the incontinence protector 401 in the longitudinal direction too.

Although the invention has been described above in connection with an incontinence protector, it can of course also be applied to sanitary towels and to diapers for children and incontinent adults.

Furthermore, the invention must not be regarded as being limited to the illustrative embodiments described herein, and instead a number of further variants and modifications are possible within the scope of the attached claims. Thus, for example, all conceivable combinations of the described illustrative embodiments are intended to be covered by the invention.

What is claimed is:

1. An absorbent article with a longitudinal direction and a transverse direction and having two side edges extending in the longitudinal direction and two end edges extending in the transverse direction, and comprising a liquid-permeable cover layer, a liquid-impermeable cover layer, and an absorption body enclosed between the two cover layers, at least one elastic member being arranged with prestressing in the crotch area of the article, extending essentially in the transverse direction of the article, between the side edges, wherein the elastic member is arranged between the liquid-permeable cover layer and the absorption body on a first surface of the absorption body, and a shaping element which is rigid to bending in the transverse direction of the article is arranged between the side edges of the article on a second surface of the absorption body, the shaping element counteracting contraction of the elastic member, the shaping element and the elastic member cooperating to form the absorbent article into a cup shape.

2. The absorbent article according to claim 1, wherein the cup shape is concave toward the user.

3. The absorbent article according to claim 1, wherein the shaping element comprises a layer of foam material.

4. The absorbent article according to claim 1, wherein the shaping element constitutes the liquid-impermeable cover layer of the article.

5. The absorbent article according to claim 1, wherein the shaping element has a resistance to deformation which remains essentially unaffected after wetting.

6. The absorbent article according to claim 1, wherein the shaping element comprises a layer of strongly compressed fibre material with a density of at least 0.1 g/cm$^3$.

7. The absorbent article according to claim 1, wherein the shaping element has bend notches.

8. The absorbent article according to claim 1, wherein the shaping element comprises at least two parts separated along the longitudinal direction of the article.

9. The absorbent article according to claim 1, wherein the shaping element has a stiffness which remains essentially unaffected after wetting.

10. The absorbent article according to claim 1, wherein a number of elastic members are arranged between the side edges of the article.

11. The absorbent article according to claim 10, wherein the elastic members are strings or bands.

12. The absorbent article according to claim 1, wherein the absorption body has bend notches.

13. The absorbent article according to claim 12, wherein the bend notches consist of cutouts in the absorption body.

14. The absorbent article according to claim 13, wherein the bend notches consist of compressions in the absorption body.

\* \* \* \* \*